United States Patent [19]

Schiff

[11] Patent Number: 4,515,587
[45] Date of Patent: May 7, 1985

[54] IAB HAVING APPARATUS FOR ASSURING PROPER BALLOON INFLATION AND DEFLATION

[75] Inventor: Peter Schiff, Cookeville, Tenn.

[73] Assignee: SMEC, Inc., Cookeville, Tenn.

[21] Appl. No.: 466,063

[22] Filed: Feb. 14, 1983

[51] Int. Cl.³ .................................... A61M 29/02
[52] U.S. Cl. .................................... 604/96; 128/344; 128/325; 128/1 D; 604/282
[58] Field of Search .......... 128/1 D, 344, 345, 303.11, 128/343, 348.1, 325; 604/166, 167, 96, 99, 100, 101, 102, 103, 282

[56] References Cited

U.S. PATENT DOCUMENTS

| 3,115,138 | 12/1963 | McElvenny | 604/133 |
| 4,141,361 | 2/1979 | Snyder | 604/133 |
| 4,261,339 | 4/1981 | Hanson | 128/1 D |
| 4,327,709 | 5/1982 | Hanson | 128/1 D |
| 4,422,447 | 12/1983 | Schiff | 128/1 D |

Primary Examiner—Stephen C. Pellegrino
Assistant Examiner—Mark Rooney
Attorney, Agent, or Firm—Louis Weinstein

[57] ABSTRACT

An intra-aortic balloon (IAB) having an elongated member expandable within said balloon to prevent total collapse of the balloon or any portion thereof during deflation. The member preventing balloon collapse, in one preferred embodiment, is stored in the catheter tube in the collapsed state and expands when moved into the balloon. In another embodiment, the member preventing deflation is arranged within the balloon and is provided with an operating member for selectively expanding and collapsing the member provided for preventing deflation. Moving the member for preventing deflation to the collapsed state permits the profile of the balloon to be significantly reduced which aids in percutaneous insertion and in removal of the balloon.

24 Claims, 9 Drawing Figures

IAB HAVING APPARATUS FOR ASSURING PROPER BALLOON INFLATION AND DEFLATION

FIELD OF THE INVENTION

The present invention relates to intra-aortic balloons (IAB's) and more particularly to means arranged within the balloon portion of an IAB for preventing premature deflation in portions thereof.

BACKGROUND OF THE INVENTION

IAB's are typically employed for assisting a weakened heart in performing its pumping function. IAB's are preferably inserted percutaneously. In order to facilitate percutaneous insertion, at least the balloon portion of an IAB is adapted to be wrapped about itself or about a stylet extending through the balloon to reduce the profile of the balloon at least during insertion and positioning thereof. Once the balloon is inserted, means are typically provided for untwisting or unwrapping the balloon to permit balloon pumping.

The unwrapped balloon is coupled to a source of pressure capable of periodically inflating and deflating the balloon in a particular timing relationship with the weakened heart to assist the heart in its pumping function. During one phase of balloon pumping, a vacuum is drawn upon the balloon causing the balloon to deflate and substantially fully collapse. Although it is extremely desirable to have the balloon collapse over substantially its entire length, it is possible that the balloon will partially collapse. For example, it is possible that the proximal end of the balloon will collapse so completely as to prevent the portion of the balloon between the distal end and the point of collapse from deflating fast enough for adequate synchronization with the heart's contraction. This condition will slow down passage of blood in the region of the aortic arch where the inflated portion of the balloon is positioned, seriously interfering with the pumping function of the heart, compromising the benefits of the balloon, and potentially causing great harm to the patient.

BRIEF DESCRIPTION OF THE INVENTION

The present invention is characterized by comprising means for preventing partial premature deflation and is either permanently positioned within the balloon or movable from the catheter portion of the balloon into the balloon to hold the balloon in at least a partially expanded state sufficient to thereby prevent the balloon from completely deflating along any small portion of its length to assure total and proper escape of the inflating gas from the entire balloon.

In one preferred embodiment, the deflation prevention member comprises an elongated resilient means capable of expanding in a generally outward radial direction, and may be contained within the catheter tube portion, preventing the member from such expansion. An operating member is provided for moving the deflation prevention member into the balloon which is significantly more yieldable in the radial direction than the catheter tube whereby the inflation prevention member expands radially outwardly to hold substantially the entire length of the balloon in a slightly expanded position. Thus, the balloon is prevented from totally collapsing along any portion thereof to assure that the gas within the balloon is substantially fully and quickly evacuated.

In another embodiment of the present invention, the deflation prevention member is arranged within the balloon and is provided with an operating member operable in a first manner for collapsing the deflation prevention member and operable in a second manner for expanding the deflation prevention member. Some embodiments of the last-mentioned preferred embodiment respectively comprise a pair of twistable helically-wound resilient members with an operating member for twisting said helical members in a first direction to contract said members in an inward radial direction and twistable in a reverse direction for expanding said helical members in an outward radial direction. The other subembodiment thereunder is comprised of an elongated undulating member having an operating member movable in a first direction for causing the undulating member to expand radially outward and movable in the reverse direction, preferably along the longitudinal axis of the catheter tube, to collapse the undulating member in the inward radial direction.

Another sub-modification of the alternative embodiment comprises of an undulating member coupled to an operating member movable in a first linear direction for collapsing the undulating member and allowing the balloon to substantially completely collapse, and movable in a second direction for expanding the undulating member in an outward radial direction for maintaining the balloon in an expanded state and preventing substantially complete collapse of any portion thereof.

OBJECTS OF THE INVENTION AND BRIEF DESCRIPTION OF THE FIGURES

It is, therefore, one object of the present invention to provide an IAB having means movable to a first position for facilitating percutaneous insertion of the balloon and movable in a second direction for preventing total collapse of the balloon during balloon pumping.

Still another object of the present invention is to provide apparatus of the character described in which the means for preventing total collapse of the balloon is movable between the balloon and the balloon catheter to facilitate pumping and balloon insertion, respectively.

Still another object of the present invention is to provide an IAB of the character described in which the means for preventing total collapse of the balloon is positioned within the balloon and is selectively extended and contracted in a radial direction by operating means accessible at a location external to the body of the patient.

The above, as well as other objects of the invention, will become apparent when reading the accompanying description and drawing in which.

DETAILED DESCRIPTION OF THE INVENTION AND PREFERRED EMBODIMENTS THEREOF

Figure 1:
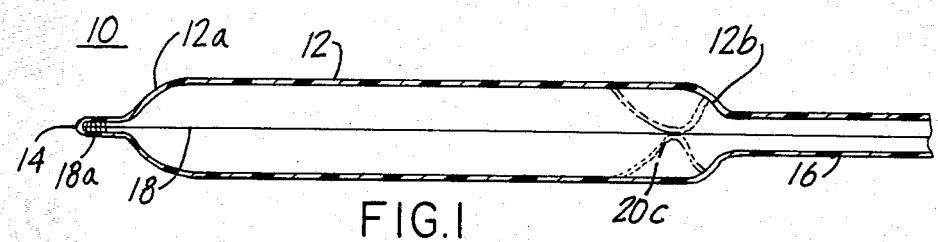
FIG. 1 shows a simplified view of a conventional intra-aortic balloon which may utilize the present invention to great advantage.

FIG. 1 shows a conventional IAB 10 comprised of a balloon 12 formed of a flexible and substantially inelastic material capable of being inflated without experiencing significant stretching when inflated under normal operating pressures.

The distal end of 12a of balloon 12 tapers as shown, terminating in a tip 14. Proximal end 12b tapers to be joined to and communicated with the hollow interior of catheter tube 16 which is connected to a source (not shown for purposes of simplicity) for providing positive and negative pressure pulses for respectively inflating and deflating balloon 12. Catheter tube 16 is of a length sufficient to properly position balloon 12 near the aortic arch while assuring that the proximal end of catheter tube 16 is accessible external to the patient.

A stylet 18 has its distal end 18a extending into and coupled with tip 14. The stylet extends through balloon 12 and catheter tube 16 and is of a length sufficient to be accessible external to the body of the patient. Stylet 18 is provided to facilitate wrapping of balloon 12 about the stylet to significantly reduce the outer diameter of balloon 12 and thereby greatly facilitate insertion of the balloon and especially through the use of a percutaneous insertion technique. Balloon 12 may either be wrapped about stylet 18 or stylet 18 may be twisted about its central axis causing tip 14 to be twisted in order to wrap balloon 12 about stylet 18. Upon proper placement of an inserted balloon 12, the balloon may be untwisted by rotation of stylet 18 in the opposite direction.

During balloon pumping, balloon 12 is substantially completely evacuated by drawing a vacuum, (i.e. negative pressure pulse) upon catheter tube 16. This will result in deflation and collapse of balloon 12. As a result of balloon collapse, the folds of the balloon material are contracted substantially toward the central axis of angular-shaped balloon 12. One possible result is the drawing together of these folds, for example in the region 20c, which may serve to effectively seal the balloon at this location, preventing the gas yet to be evacuated from balloon 12 and in the region between tip 14 and collapsed portion 20c, from being captured in the balloon due to the aforesaid seal thereby allowing this last-mentioned portion of the balloon to retain an inflated or partially inflated condition. This nonuniform contraction of balloon 12 may have a degrading and even harmful effect upon balloon pumping and endanger the life and well-being of the patient.

The present invention overcomes the disadvantages of the prior art through apparatus embodying the principles of the present invention and alternative embodiments of which are shown in FIGS. 2a through 5.

Figure 2A:
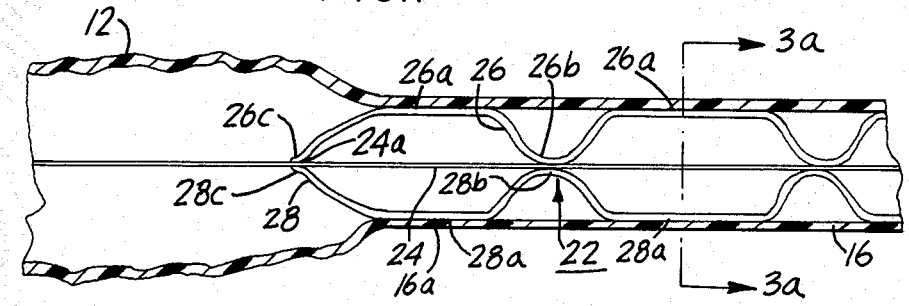
FIGS. 2a and 2b are enlarged sectional views showing portions of an intra-aortic balloon incorporating one embodiment of the present invention.

FIG. 2a shows the portion of catheter tube 16 incorporating proximal end 16a which is joined with balloon 12. The assembly 22 for preventing total collapse of balloon 12 is comprised of an elongated stylet 24, which may be stylet 18 or a stylet separate and independent from stylet 18. A pair of elongated, undulating, resilient members 26 and 28 are arranged to lie substantially along an imaginary diameter of catheter 22 and have an undulating configuration made up of alternating peaks 26a-28a and valleys 26b-28b which collectively define the undulating shape. Left-hand ends 26c, 28c of members 26 and 28 are joined to stylet 24 at a point 24a. Stylet 24 extends to the right and is of a length sufficient to extend beyond the proximal end (not shown) of catheter tube 16, accessible at a location exterior to the body of the patient.

Assembly 22 is normally positioned within catheter tube 16 and preferably has a length slightly less than the length of balloon 12. When retained within catheter tube 16, the cylindrical wall of catheter tube 16 exerts a force upon members 26 and 28 sufficient to significantly flatten at least the peak portions 26a, 28a of resilient members 26 and 28 in a manner shown in FIG. 2a. When assembly 22 is stored within catheter tube 16, balloon 12 may be substantially tightly wrapped about stylet 18 to significantly reduce its outer diameter and thereby provide a low profile for facilitating insertion into the body.

After the balloon 12 is inserted and properly positioned within the aortic arch, and before initiating balloon pumping, stylet 24 is urged toward the left as shown by arrow 32 moving the entire assembly to the left and out of catheter tube 16 into balloon 12. As shown best in FIG. 2b, the forces imposed upon members 26 and 28 by catheter tube 16 are substantially relieved as members 26 and 28 are moved into balloon 12. Noting FIG. 2b, the flattened portions of peaks 26a, 28a, are free to expand outwardly to assume a natural curvature as shown at 26a', 28a', in FIG. 2b, urging balloon 12 into an expanded condition to a degree sufficient to prevent total collapse of the balloon in the manner described in connection with balloon portion 20c, shown in FIG. 1. The spacing between adjacent peaks 26a', 28a' of members 28 and 26 and the distance of each peak 26a', 28a' from stylet 24 is sufficient to prevent balloon 12 from totally collapsing in the region of the pair of adjacent valleys 26b, 28b. The peaks 26a and 28a may expand to the inside diameter of the balloon 12, or to a far lesser diameter equal to a fraction of the balloon diameter. In either eventuality, the balloon is not permitted to experience a totally collapsed state.

In the event that it is desired to remove IAB 10 from the body, stylet 24 may be pulled to the right as shown by arrow 34 (FIG. 2b) to permit the balloon to be twisted and wrapped about stylet 18 or, alternatively, to permit the balloon to be substantially completely collapsed to facilitate removal thereof. FIG. 3c shows a sectional view of assembly 22. The adjacent valley portions 26b, 28b are provided with semicircular configurations 26c, 28c for receiving and supporting stylet 24 which is preferably a hollow elongated tube. Stylet 18 is positioned within the interior of tube 24 and is freely movable therein.

Figure 3C:
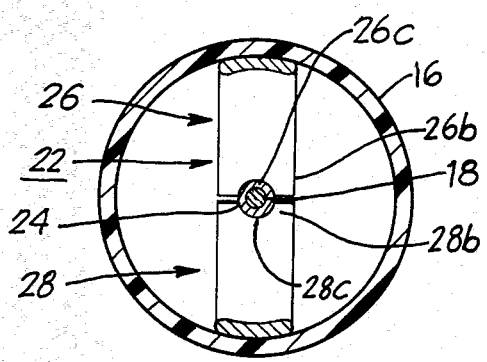
FIGS. 3a and 3b show end section and side section views of portions of an IAB incorporating another preferred embodiment of the present invention.
Figure 3A:
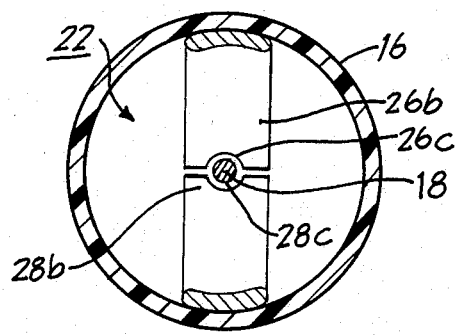
Figure 3B:
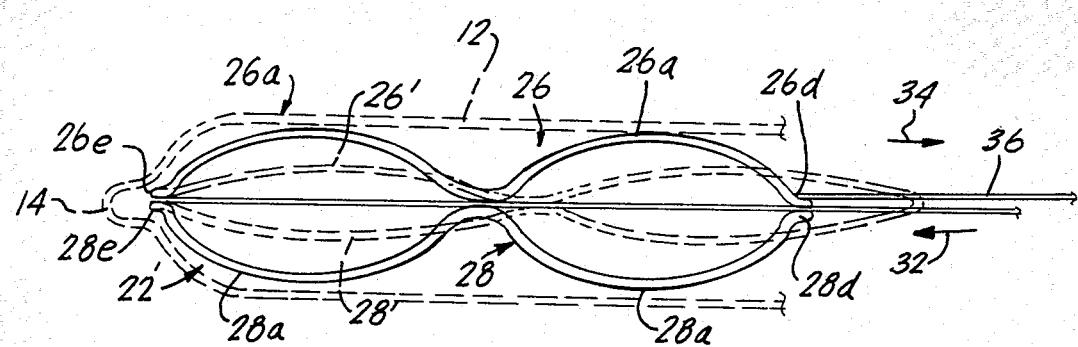

As another alternative embodiment in FIG. 3b, proximal ends 26d, 28d of resilient members 26 and 28 may be coupled to a stylet 36 accessible from a position external to proximal end of catheter 16 and external to the body of the patient. The semicircular portions of the valleys 26b, 28b slidably receive and are guided by stylet 18. Movement of operating member 36 in the direction shown by arrow 32 moves assembly 22' shown in FIG. 3b from catheter tube 16 into balloon 12 to cause the flattened portions of peaks 26a, 28a which are contracted in this manner by the smaller inner diameter of catheter tube 16, to be expanded and thereby assume their natural curvature when assembly 22' is moved into balloon 12.

As another alternative of the embodiment 22' shown in FIG. 3b, the distal ends 26e, 28e of members 26 and 28 may be securely fastened to stylet 18 at a location substantially in or immediately adjacent to tip 14, shown in FIG. 1. In this embodiment, assembly 22' is not stored within catheter tube 16 but is permanently positioned within balloon 12. Collapse of the resilient members 26 and 28 of assembly 22' is accomplished by means of urging operating member 36 toward the right as shown by arrow 34, causing members 26 and 28 to assume the dotted line configuration 26', 28'. When it is desired to maintain balloon 12 in the expanded state, operating member 36 is released, i.e., allowed to move toward the left as shown by arrow 32 under the resilient spring force of members 26 and 28, said members resuming their natural undulating configuration, and thereby holding balloon 12 in a slightly expanded position and preventing total collapse.

Figure 4:
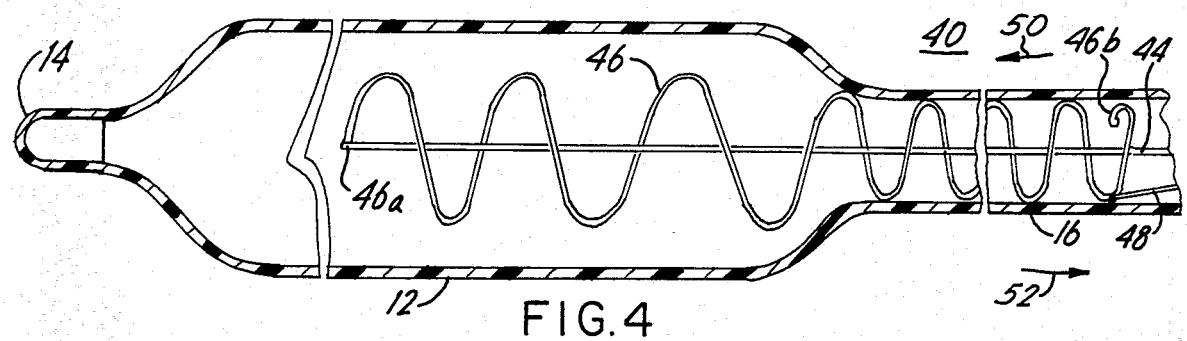
FIG. 4 shows a sectional view of an IAB incorporating another preferred embodiment of the present invention.

FIG. 4 shows another embodiment 40 in which the assembly for preventing collapse of the balloon 12 comprises an elongated helical spring 46 normally stored within catheter tube 16 and movable by means of an operating member (or members) such as stylets 44 and 48.

As was described hereinabove, when preparing the IAB for percutaneous insertion, helical spring 46 is retained within catheter 16 to facilitate fairly tight wrapping of the balloon 12 about the longitudinal axis after the IAB.

After the IAB is inserted and properly positioned within the body, stylet 44 is moved in the direction shown by arrow 50 urging the helical spring to the left and moving the spring from its storage position within catheter tube 16 and into balloon 12. The small inner diameter of catheter tube 16 retains spring 46 in the reduced diameter condition. As spring 46 leaves catheter tube 16 and enters into balloon 12, the forces exerted on the helical spring are released, enabling helical spring 46 to expand and thereby maintain balloon 12 in an expanded state and preventing both total and partial collapse thereof. The free end 46b of coil 46 is provided to prevent accidental withdrawal of coil 46 from balloon 12 to catheter tube 16.

In the event that it is desired to remove the IAB from the body, the spring 46 may be returned to catheter tube 16 by moving stylets 48 and/or 44 to the right as shown by arrow 52 to permit balloon 12 to be substantially fully collapsed and wrapped about its longitudinal axis to facilitate the wrapping of the balloon 12 about its longitudinal axis. The embodiment of FIG. 4 may incorporate stylet 18 as shown best in FIG. 4a wherein the distal end 46a of spring member 46 is provided with an eyelet 52 through which stylet 18 passes. Stylet 44 is coupled to eyelet 52. Stylet 18 cooperates with eyelet 52 to guide the movement of helical spring 46 substantially along the central axis of catheter tube 16 and balloon 12 as helical spring 46 is moved between catheter tube 16 and balloon 12.

Figure 5:
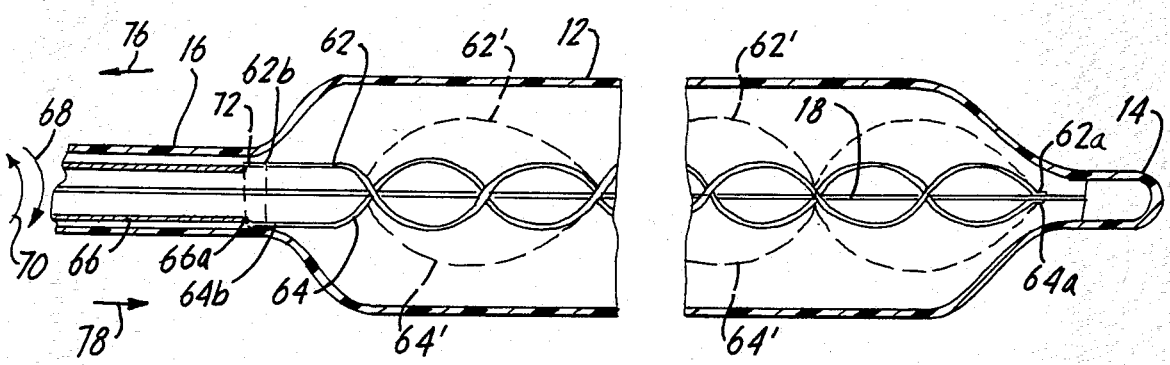
FIG. 5 shows a sectional view of an IAB incorporating still another embodiment of the present invention.

FIG. 5 shows still another embodiment of the present invention wherein the assembly for preventing total collapse of balloon 12 comprises a pair of helically wound resilient members 62 and 64 whose distal ends 62a and 64a are secured to stylet 18. Helically wound members 62 and 64 extend substantially over the length of balloon 12. The proximal ends 62b, 64b of helical members 62 and 64 lie at opposite ends of an imaginary diameter at the distal end 66a of an elongated tube 66 whose proximal end (not shown) is accessible at a position external to the patient. The members 62 and 64 are preferably tightly wound preparatory to insertion of the IAB to facilitate wrapping of balloon 12 about its central axis. After the balloon has been inserted and properly positioned within the body of the patient, tube 66 is rotated in the first direction as shown by arrow 68 causing the "untwisting" of members 62 and 64, whereby these members assume the expanded configuration as shown by the dotted line resilient members 62' and 64'. The expanded position of members 62 and 64 substantially prevent total collapse and thereby assure proper deflation of balloon 12.

Preparatory to removal of the IAB and preparatory to insertion thereof, tube 66 may be rotated in the direction shown by arrow 70 to significantly reduce the outer diameter of helical members 62 and 64 to facilitate wrapping of balloon 12 about its longitudinal axis.

As an alternative embodiment, the proximal ends 62b, 64b of resilient members 62 and 64 may be secured to a ring 72 shown in dotted fashion in FIG. 5, and anchored within the neck of catheter tube 16. By rotating stylet 18 in a direction shown by arrows 68 and 70, members 62 and 64 may be respectively enlarged and decreased in outer diameter to facilitate the balloon pumping and balloon insertion (and removal) operations.

Although not shown for purposes of simplicity, it should be understood that the actual diameters of the helical members 62 and 64 may be smaller or larger than those depicted for example as shown in FIG. 5, for both balloon pumping and balloon insertion (removal) operations, and the positioning of members 62 and 64 shown in FIG. 5 is primarily for purposes of better understanding the invention.

For IAB's in which stylet 18 is made twistable to respectively wrap and unwrap balloon 12 about its longitudinal axis, the distal ends 62a, 64a, of helical members 62 and 64 may be anchored within tip 14 and displaced from stylet 18 to permit rotation of stylet 18 independently of the twisting and untwisting of the resilient helical members 62 and 64.

As a still further embodiment, the helical members 62 and 64, instead of being twisted in opposing directions to be expanded and contracted, may be anchored at distal ends 62a, 64a, and be pulled in a direction of arrow 76 to reduce their outer diameter and alternatively may be released, i.e. free to move in the direction shown by arrow 78 to cause the helical members 62, 64, to assume the enlarged diameter configuration shown by dotted line positions 62', 64'. The operating member may thus be an elongated stylet for respectively stretching and releasing helical members 62 and 64 in a manner similar to the operation of the undulating members 26 and 28 shown, for example, in FIGS. 2a and 2b.

A latitude of modification, change and substitution is intended in the foregoing disclosure, and in some instances some features of the invention will be employed without a corresponding use of other features. Accordingly, it is appropriate that the appended claims be construed broadly and in a manner consistent with the spirit and scope of the invention herein.

What is claimed is:

1. An intra-aortic balloon assembly comprising:
an inflatable balloon formed of a non-stretchable plastic material and having a distal end terminating in a tip and having an open proximal end and a longitudinal axis extending between the proximal end and the tip;

an elongated catheter tube having a distal end communicating with and air-tightly joined to the open proximal end of said balloon and having a proximal end for receiving positive and negative pressure pulses for selectively inflating and deflating said balloon;

elongated resilient means located within said balloon assembly for selectively preventing collapse of said balloon;

operating means extending into said catheter tube and coupled to said resilient means; said operating means being movable in a first direction for effecting expansion of said resilient means to prevent collapse of said balloon and movable in a second direction for effecting compression of said resilient means to enable said balloon to substantially fully collapse.

2. The balloon assembly of claim 1 wherein said operating means extends beyond and is accessible from the proximal end of said catheter tube.

3. The balloon assembly of claim 1 wherein said operating means comprises linearly movable means for moving said resilient means in said first direction from a position in said catheter tube into said balloon and moving said resilient means in said second direction from said balloon to said catheter tube.

4. The balloon assembly of claim 3 wherein said resilient means is comprised of at least one spring.

5. The balloon assembly of claim 4 wherein said spring comprises at least one helical spring.

6. The balloon assembly of claim 4 wherein the inner diameter of the balloon in the inflated state is greater than the inner diameter of said catheter tube;
said resilient means having at least a portion thereof which expands upon entering into said balloon.

7. The balloon assembly of claim 6, wherein the portion of the resilient means which expands is adjacent to the proximal end of the balloon and prevents the resilient means from reentering said catheter tube due to the expansion of said portion of the resilient means.

8. The balloon assembly of claim 7 wherein said resilient means is a helical spring having at least a portion thereof which is expandable in a radial direction as said portion enters into said balloon.

9. The balloon assembly of claim 7 wherein said resilient means is comprised of at least one elongated undulating expandable resilient member which expands in a direction away from the longitudinal axis of said balloon to expand said balloon when said resilient member moves from said catheter tube into said balloon.

10. The balloon assembly of claim 9 wherein said resilient member has an elongated ribbon-like configuration performed and pretreated to assume its undulating configuration.

11. The balloon assembly of claim 10 wherein said undulating member is formed of a resilient plastic material.

12. The balloon assembly of claim 10 wherein said undulating member is formed of a resilient metallic material.

13. The balloon assembly of claim 1 wherein said resilient means comprises a plurality of elongated strips and resilient compressible means arranged between said strips and being expandable when the resilient means is moved into said balloon to increase the separation distance between said strips and thereby retain the balloon in an expanded state.

14. The balloon assembly of claim 13 wherein said resilient compressible means comprise spring means.

15. The balloon assembly of claim 14 wherein said spring means is an elongated undulating resilient spring member.

16. The balloon assembly of claim 15 wherein said spring means comprises a plurality of substantially V-shaped resilient spring members positioned between said strips for increasing the separation distance between said strips when the resilient means enters into said balloon.

17. The balloon assembly of claim 1 wherein said resilient means comprises at least one resilient, elongated expandable member positioned in said balloon and having a distal end joined to said tip and a proximal end extending through said balloon and into said catheter tube;
said operating means comprising operating member coupled to the proximal end of said expandable member and movable in a first direction for expanding said expandable member to expand said balloon toward its inflated condition and movable in a second direction to contract said expandable member.

18. The balloon assembly of claim 17 wherein said expandable member comprises an elongated helical member movable to an expanded condition when twisted in a first direction and being contracted when twisted in a second direction.

19. The balloon assembly of claim 17 wherein said expandable member comprises at least a pair of helical members movable to an expandable condition when twisted in a first direction and being contracted when twisted in a second direction.

20. The balloon assembly of claim 17 wherein said expandable member comprises an undulating member movable in a first direction to expand said balloon and movable in a second direction to contract.

21. The balloon assembly of claim 17 wherein said operating member comprises an elongated flexible member having a distal end joined to the proximal end of said expandable member and having a proximal end accessible from the proximal end of said catheter tube for operating said expandable means.

22. The balloon assembly of claim 21 wherein said operating member is rotatable to operate said expandable member.

23. The balloon assembly of claim 21 wherein said operating member is linearly movable to operate said expandable member.

24. The operating member of claim 1 further comprising a proximal end thereof being extendable to prevent accidental withdrawal of the deflection prevention means from the balloon to prevent accidental movement of the deflation prevention means back into the catheter tube.

* * * * *

UNITED STATES PATENT AND TRADEMARK OFFICE
CERTIFICATE OF CORRECTION

PATENT NO. : 4,515,587

DATED : May 7, 1985

INVENTOR(S) : Peter Schiff

It is certified that error appears in the above-identified patent and that said Letters Patent is hereby corrected as shown below:

In the Title page, line 5, change "Assignee: SMEC, Inc., Cookeville, Tenn." to --Assignee: None--.

Figure 2B:
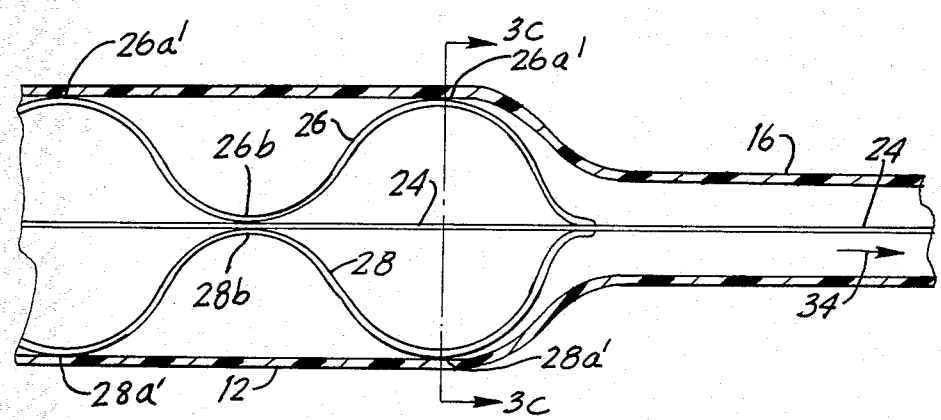

Column 2, after line 65 insert paragraph --Fig. 3c is a sectional view of the balloon structure of Fig. 2b looking in the direction of arrows 3c-3c.--.

Figure 4A:
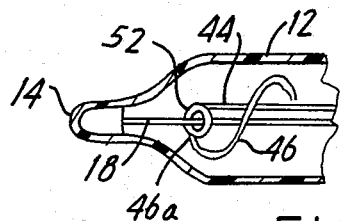
FIG. 4a is a sectional view of an IAB showing an alternative arrangement for guiding the spring of FIG. 4.

Column 3, after line 3 insert paragraph --Fig. 4a is a sectional view of an IAB showing an alternative arrangement for guiding the spring of Fig. 4.--.

Column 3, line 51 change "20c," to --20c--.

Column 3, line 52 after "seal" insert --,--.

Column 5, line 6 before "shown" insert --as--.

Claim 17, line 7 before "operating" (second occurence) insert --an--.

Signed and Sealed this

Fifth Day of November 1985

[SEAL]

*Attest:*

*Attesting Officer*

DONALD J. QUIGG

*Commissioner of Patents and Trademarks*